United States Patent [19]

Davidson

[11] Patent Number: Plant 7,706

[45] Date of Patent: Nov. 12, 1991

[54] HYBRID TEAROSE PLANT NAMED 'SMOOTH PRINCE'

[76] Inventor: Harvey D. Davidson, #3 El Verano Rd., Orinda, Calif. 94563

[21] Appl. No.: 536,357

[22] Filed: Jun. 11, 1990

[51] Int. Cl.[5] ..... A01H 5/00

[52] U.S. Cl. ..... Plt./20

[58] Field of Search ..... Plt. 20, 21, 11

[56] References Cited

U.S. PATENT DOCUMENTS

P.P. 382 4/1940 Grillo ..... Plt. 20

*Primary Examiner*—Howard J. Locker

[57] ABSTRACT

A new rose variety of the Hybrid Tea class characterized by having large well formed medium red flowers on a thornless bush with disease resistant glossy foliage.

1 Drawing Sheet

The present invention relates to a new and distinctive variety of rose plant of the Hybrid Tea class, which was originated by my crossing 'Smooth Sailing' as the seed parent with 'Old Smoothie' (U.S. Plant Pat. No. 3,098) as the pollen parent.

Among the novel characteristics possessed by the new variety which distinguish it from its:

(a) Parents and all other varieties of which I am aware are:
- (1) A plant which is thornless throughout.
- (2) A flower with medium red petals both inside and out, which opens with distinctive petal symmetry.
- (3) Very rapid flowering cycles.
- (4) Excellent keeping quality as a cut flower.
- (5) A vigorous upright plant of medium height.

(b) Seed parent: Grandiflora, cream, very tall.
Pollen parent: Hybrid tea, red, semi-thornless.

Asexual reproduction of the new rose variety by budding, as performed at Tulare, Calif. shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in the color description herein refers to plate numbers in the aforementioned color chart, e.g., "53A" is plate "53A" of The Royal Horticultural Society Colour Chart.

American Rose Society Registration commercial appellation: 'Smooth Prince'.
Parentage: Seedling.
*Seed parent.*—'Smooth Sailing'.
*Pollen parent.*—'Old Smoothie'.
Class: Hybrid Tea.

The following observations are made of specimens grown outdoors in Contra Costa County, Calif., in the month of October.

FLOWER

Blooming habit:

A. Bud:
- (1) *Size.*—Large.
- (2) *Form.*—Globular.
- (3) *Sepals.*—36 to 40 mm in length; 12 to 15 mm extension beyond bud; No serration shown on sepal edges. Generally 1 out of 5 sepals shows 2 appendages on each side of 1 to 3 mm length; light cotton matting on inner surface of sepals; fine light cover hairs on outer surface. Color before breaking — 144A; when turned down — 148B.
- (4) *Peduncle.*—Length — 5.5 cm; Surface — smooth, no prickles or hairs; Strength — stiff, slight curvature. Color — 144A.
- (5) *Color.*—When sepals first divide — outside petals 53B; inside petals 53B shading to 53C.

B. Bloom:
- (1) *Size.*—Average when open — 12 cm.
- (2) *Borne.*—Usually singly; Occasionally 3 to 4 per stem.
- (3) *Form.*—Cupped; flat center; moderately full; fully open at maturity.
- (4) *Petalage.*—Average number — 26 to 28.
- (5) *Color.*—Early open — inside surface 53B; outside surface 53C. Aging — inside surface 63A, outside surface 57B.

C. Petals:
- (1) *Texture.*—Thick.
- (2) *Appearance.*—Satiny on both inside and outside.
- (3) *Form.*—Broad— to 5 cm width; base to upper edge — 5.5 to 6 cm; round; pointed center.
- (4) *Arrangement.*—Regular at all stages.
- (5) *Petaloids in center.*—Average 4 to 6.
- (6) *Persistence.*—Drop off cleanly.
- (7) *Fragrance.*—Light.
- (8) *Lasting quality.*—Long lasting on bush; very good cut flower.

REPRODUCTIVE ORGANS

A. Stamen:
- (1) *Arrangement.*—Regularly arranged around styles.
- (2) *Number.*—Average — 102 to 106.
- (3) *Length.*—Average — 6 to 10 mm.
- (4) *Filaments.*—Color — 62A.

(5) *Anthers.*—Color — 23B.
(6) *Pollen.*—21B.

B. Pistill:
(1) *Styles.*—Covered fine white hairs; color 54B; number 72–76.
(2) *Stigma.*—Color — Close to 8D.
(3) *Ovary.*—Average 1 cm diameter; to 12 mm depth.

C. Hips: Will set few seed only with own pollen, however rarely.
(1) *Shape.*—Oblong; to $2\frac{1}{2}$ cm diameter, to $2\frac{3}{4}$ cm depth.
(2) *Color.*—Near 26A.
(3) *Seed.*—Average 1 to 4 per hip, do not protrude.

PLANT

A. Form: Upright.
B. Growth: Vigorous; medium height — average 1.25 meters.
C. Foliage: Compound of 3 to 5 leaflets on bloom stem; 5 to 7 leaflets on main canes.
(1) *Size.*—Large.
(2) *Quantity.*—Stems well covered.
(3) *Color.*—New foliage upper side 144A, under side 178A. Old foliage upper side 147A, under side 147B.

(4) *Shape.*—Oval to rounded with center pointed.
(5) *Texture.*—Upper side — leathery, glossy. Under side — smooth, dull.
(6) *Edge.*—Moderate serration on outer edge. Average 4 to 6 points per 1 cm, with up to 1 mm peak.
(7) *Rachis.*—Slight glandular hair on upper side; generally smooth on lower side, on rare occassions 1 to 3 prickles to 2 mm length.
(8) *Stipules.*—Average length 1.5 cm; auricle to 5 mm.

D. Resistance to disease: Mildew, rust and blackspot — very good.
E. Wood:
*New wood.*—Color 144B, slightly shaded 176C; Bark — smooth.
*Old wood.*—Color 144A, shading to near 174A; Bark — smooth.
F. Thorns:
(1) *Thorns.*—None.
G. Winter hardiness: Good.

I claim:

1. A new and distinct thornless variety of rose plant of the Hybrid Tea class, substantially as shown and described.

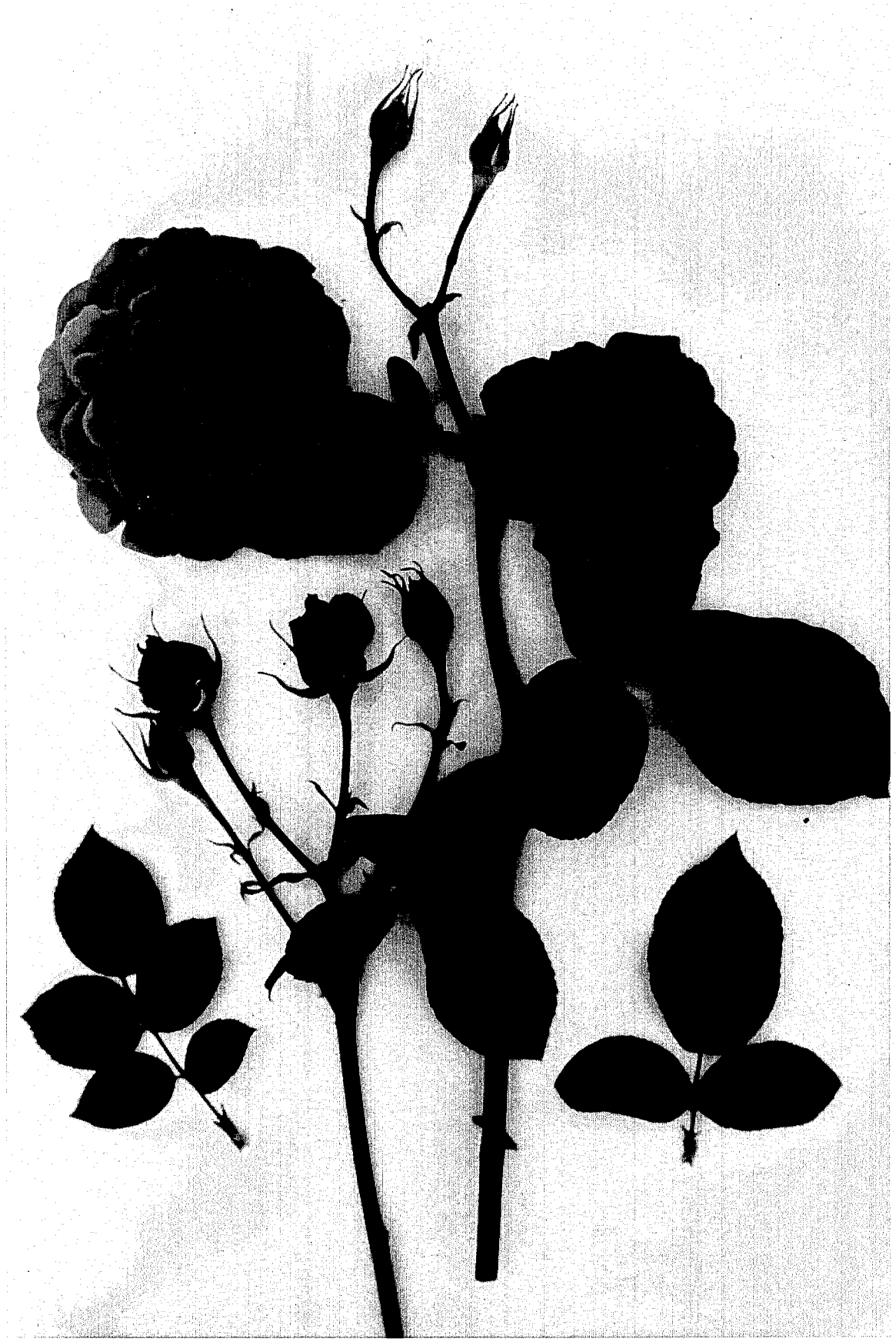

* * * * *